United States Patent [19]

Davis

[11] Patent Number: 4,707,480
[45] Date of Patent: Nov. 17, 1987

[54] METHOD FOR STABILIZING A DETRUSOR MUSCLE WHILE INCREASING DETRUSOR MUSCLE STRENGTH

[75] Inventor: William M. Davis, Tucson, Ariz.

[73] Assignee: United Pharmaceuticals, Inc., Tucson, Ariz.

[21] Appl. No.: 783,311

[22] Filed: Oct. 3, 1985

Related U.S. Application Data

[63] Continuation of Ser. No. 485,056, Apr. 14, 1983, abandoned.

[51] Int. Cl.$^4$ .................. A61K 31/21; A61K 31/535; A61K 31/445
[52] U.S. Cl. .................................. 514/228; 514/317; 514/513; 514/906
[58] Field of Search ................ 514/513, 906, 317, 228

[56] References Cited

U.S. PATENT DOCUMENTS

| | | | |
|---|---|---|---|
| 2,390,555 | 12/1945 | Richardson | 544/158 |
| 2,510,773 | 6/1950 | Clinton | 260/455 R |
| 4,432,977 | 2/1984 | Davis | 514/513 |

OTHER PUBLICATIONS

Physician's Desk Reference (PDR) 31st ed., pp. 1014–1015 (1977).
Dorland's, Illustrated Medical Dictionary, 23d ed., pp. 374 and 876 (1962).
Kukes et al., CA 92: 1045263 (1976).
Morton et al., CA 83: 557a (1972).
Medical World News, "Muscle Drug Slows Wound Contraction", (Mar. 1974), p. 74A.
Maaden et al., "Contraction of . . . Antagonist", 8 Surgery, pp. 31–38 (1974).
Morton et al., "Effect of Local Smooth Muscles . . . ", Surgical Forum vol. XXIII (1972).
McDonald, "Clinical Evaluation of Trocinate and Antispasmodic", J. Missouri State Med Assoc., (48)(9) p. 18 (1951).
Ramsey et al., J. Pharmacol. and Exper. Therapeutics, vol. 39, No. 2 (Feb. 1947), pp. 131–146.
Med. World News, Muscle Drug Slows Wound Contraction", p. 74A (Mar. 1974).
Thackston et al., J. of Urology, vol. 73, No. 3, pp. 487–493 (1955).

Primary Examiner—Albert T. Meyers
Assistant Examiner—F. Krosnick
Attorney, Agent, or Firm—Austin R. Miller

[57] ABSTRACT

A method for inhibiting unplanned or premature detrusor muscle contractions while at the same time increasing the force of contraction of the detrusor muscle is provided. The method comprises administering to the patient a di-N-substituted aminoethyl ester of diphenylthioacetic acid having the formula:

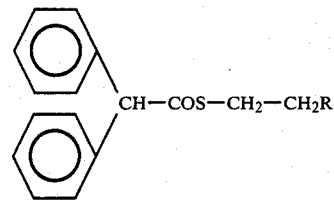

in which R represents a disubstituted amino radical of the group consisting of the diethylamino group, the morpholino group or the piperidino group.

6 Claims, 4 Drawing Figures

METHOD FOR STABILIZING A DETRUSOR MUSCLE WHILE INCREASING DETRUSOR MUSCLE STRENGTH

This application is a continuation of application Ser. No. 485,056, filed Apr. 14, 1983, now abandoned.

BACKGROUND OF THE INVENTION

1. Field of the Invention

This invention relates to a novel method of inhibiting detrusor muscle spasticity while simultaneously increasing the force of normal detrusor muscle contraction. Such an invention has many novel applications including but not limited to the treatment of patients suffering from unstable bladder conditions.

2. Description of the Prior Art

The human bladder is composed of four coats; serous, muscular, submucous and mucous. The muscular coat consists of three layers of unstriped muscular fiber: an external layer, composed of fibers having for the most part a longitudinal arrangement; a middle layer in which the fibers are arranged, more or less, in a circular manner; and an internal layer, in which the fibers have a general longitudinal arrangement. In the external longitudinal layer at the sides of the bladder, the muscle fibers are arranged obliquely and intersect one another. This layer is called the detrusor muscle.

Thiphenamil hydrochloride is a class of compounds comprising a di-N-substituted aminoethyl ester of diphenylthioacetic acid having the formula:

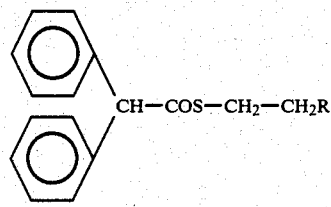

in which R represents a disubstituted amino radical of either the diethylamino group, the morpholino group or the piperidino group.

The prior uses for thiphenamil hydrochloride center around its use as an anti-spasmodic agent in the upper and lower gasto-intestinal tract for pylorospasm, spasm associated with the gallbladder and common bile duct, as well as diarrhea and the irritable bowel syndrome. Prior art uses also include treatment of ureterospasm and bladder irritation.

There have been further reports that thiphenamil hydrochloride has been successfully used for the treatment of bronchospasm.

Thiphenamil hydrochloride is a well-known compound and is described in detail in U.S. Pat. No. 2,390,555 to Richardson, incorporated herein by reference. Additional methods of making thiphenamil hydrochloride are described in U.S. Pat. No. 2,510,773 to Clinton.

The term "detrusor instability" generally refers to the condition wherein the bladder spontaneously contracts and empties before the patient is ready.

Generally, the following compounds have been used for the pharmacological treatment of detrusor instability: "URISPAS" (flavoxate hydrochloride) which is a smooth muscle relaxant; "DITROPAN" (oxybutynin chloride) an anti-cholinergic used for the relief of neurogenic bladder symptoms; and "BANTHINE" (methantheline bromide) an anti-cholinergic and anti-spasmodic drug. For the most part, the above listed and other derivatives of atropine are unpredictable in their effect on bladder instability. In addition to their rather poor successful treatment record, anti-cholinergic compounds produce undesirable side effects such as dryness of the mouth, dilation of the pupils and slowed heartbeat.

In the uses of thiphenamil hydrochloride as a smooth muscle relaxant it has generally been assumed that the drug relaxes and inhibits the ability of smooth muscles to contract. This phenomenon has been shown in a number of studies:

1. STUDIES ON THE PHARMACOLOGY OF BETA-DIETHYLAMINOETHYLDIPHENYL-THIOACETATE, A SYNTHETIC ANTISPASMODIC, Ramsey & Richardson, J. Pharm. & Exp. Th., February 1947, pp. 131–142.
2. CLINICAL EVALUATION OF TROCINATE, AN ANTISPASMODIC, MacDonald, J. Missouri Medical Association, September 1951, pp. 685–6.
3. USE OF ANTISPASMODICS IN TREATMENT OF SPASTIC URETERITIS, Thackston et. al., J. Urology, March 1955, pp. 487–493.
4. EFFECT OF A LOCAL SMOOTH MUSCLE ANTAGONIST ON WOUND CONTRACTION, Morton et. al., Surg. Forum, Vol. 23, 1972.
5. MUSCLE DRUG SLOWS WOUND CONTRACTION, Medical World News, March 1974, p. 74A.
6. CONTRACTION OF EXPERIMENTAL WOUNDS I. INHIBITING WOUND CONTRACTION BY USING A TOPICAL SMOOTH MUSCLE ANTAGONIST, Madden et. al., Surgery, July 1974, pp. 8–15.

As a result of these and other studies, persons skilled in the art generally expect the force of the smooth muscle contractions to be greatly diminished after administering thiphenamil hydrochloride.

There has been a need in the pharmaceutical art for a drug which inhibits involuntary detrusor contractions while at the same time increasing the strength of voluntary detrusor contractions.

Thus, it is an important object of the present invention to provide a method for inhibiting unplanned or premature muscle contraction of the detrusor muscle while at the same time increasing the force of voluntary contraction of the detrusor muscle.

It is yet another important object of the present invention to provide such a method which is safe for use on human patients, particularly sensitive patients such as glaucoma patients, without subjecting the patient to the undesirable side effects of anti-cholinergic drugs, for example dryness of the mouth, dilation of the pupils and slowed hearbeat.

It is another important object of the present invention to provide such a method of inhibiting unplanned or premature muscle contraction while at the same time increasing the force of the detrusor muscle contraction without leaving or accumulating any foreign substances in the human body tissues.

SUMMARY OF THE INVENTION

These and other objects are met in the novel method for inhibiting unplanned or premature detrusor muscle contractions while at the same time increasing the force of contraction of the detrusor muscle comprising the administration of a di-N-substituted aminoethyl ester of diphenylthioacetic acid having the formula:

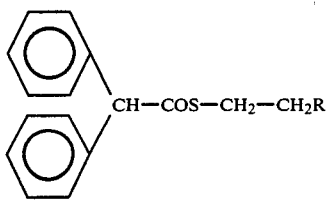

in which R represents a disubstituted amino radical of the group consisting of the diethylamino group, the morpholino group or the piperidino group.

DESCRIPTION OF THE PREFERRED EMBODIMENTS

It is evident from the experimental results which follow that thiphenamil hydrochloride inhibits involuntary detrusor muscle contraction while at the same time increasing the force of voluntary detrusor muscle contractions. Apparently, the combined action of inhibiting detrusor spasticity while increasing the force of detrusor contraction is a unique property of thiphenamil hydrocloride and is an unknown action of any other compound.

The advantage of this effect of thiphenamil hydrochloride is that involuntary detrusor muscle contraction is inhibited thereby giving the patient effective bladder control. Furthermore, because the strength of the detrusor muscle contraction is increased, there is a more complete emptying of the bladder, even in cases where there is a partial obstruction such as in a prostatic obstruction generally encountered in older patients suffering from prostatic hypertrophy.

The experimental results reveal that thiphenamil hydrochloride acts as an effective detrusor spasticity inhibitor and detrusor force of contraction increaser in a dosage range of from about 0.7 to about 11.4 mg/kg of body weight. A preferred dosage is in the range of from about 1.4 to about 5.7 mg/kg of body weight. A still more preferred dosage range is from about 2.8 to about 5.7 mg/kg of body weight.

Thiphenamil hydrochloride can be administered orally, typically in tablets of 100–400 mg or by intravenous injection.

Because thiphenamil hydrochloride slowly hydrolyzes in water, it is generally not used as a serum or suspension. It is possible however to encapsulate microspheres of thiphenamil hydrochloride in the form of a liquid suspension for administration to patients.

The invention is further disclosed by means of the following examples which are intended only as illustrations and which in no way limit the invention.

EXAMPLES

Urodynamic studies were performed on 20 women having a mean age of $28\pm7$ years. These studies incorporated water cystometrogram, UPP, and isometric tests. Control urodynamic testing without use of thiphenamil hydrochloride was undertaken in all subjects. The effects of a single dose of 400 mg and a single dose of 800 mg of thiphenamil hydrochloride given orally were compared with the control value for each subject. Specifically, the measurements taken included bladder capacity, residual volume, maximum detrusor voiding pressure, and isometric contractility during bladder filling and at bladder capacity.

The results of these experiments are shown in Tables I–IV.

The experimental results show no significant increase in bladder capacity and a decrease in the detrusor muscle contractility of from $41.3\pm15.3$ cm $H_2O$ to $37.2\pm16.0$ cm $H_2O$.

The test results further demonstrate that the isometric detrusor pressure during the filling phase of the bladder significantly increases from $36.1\pm26.9$ cm $H_2O$ to $63.0\pm27.1$ cm $H_2O$.

Figure 1:
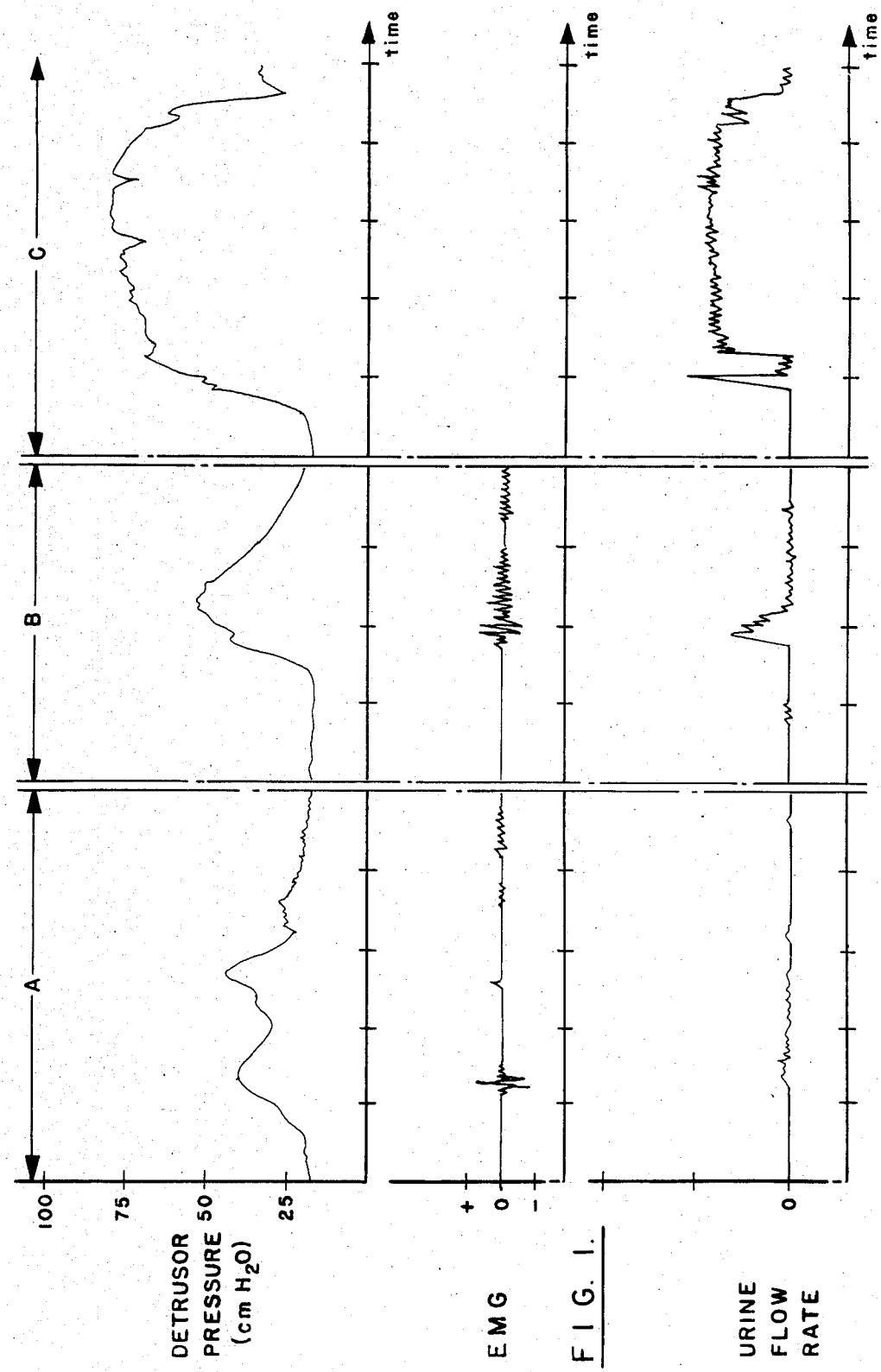
FIG. 1 is a graph showing data taken from a subject with a normal detrusor under control conditions.

Referring to FIG. 1, data is shown taken from a subject having normal detrusor activity. The parameters measured include isometric detrusor pressure during bladder filling and while voiding under control conditions, EMG and urine flow rate. Typical segments of a polygraph recording were obtained at a bladder volume of 100 ml (segment A), 200 ml (segment B) and the voiding at 300 ml (segment C). The parameters shown are detrusor pressure in cm $H_2O$. EMG (electromyogram) recording showing muscle electrical activity and urine flow rate. This subject exhibited no detrusor instability during the measurements.

Figure 2:
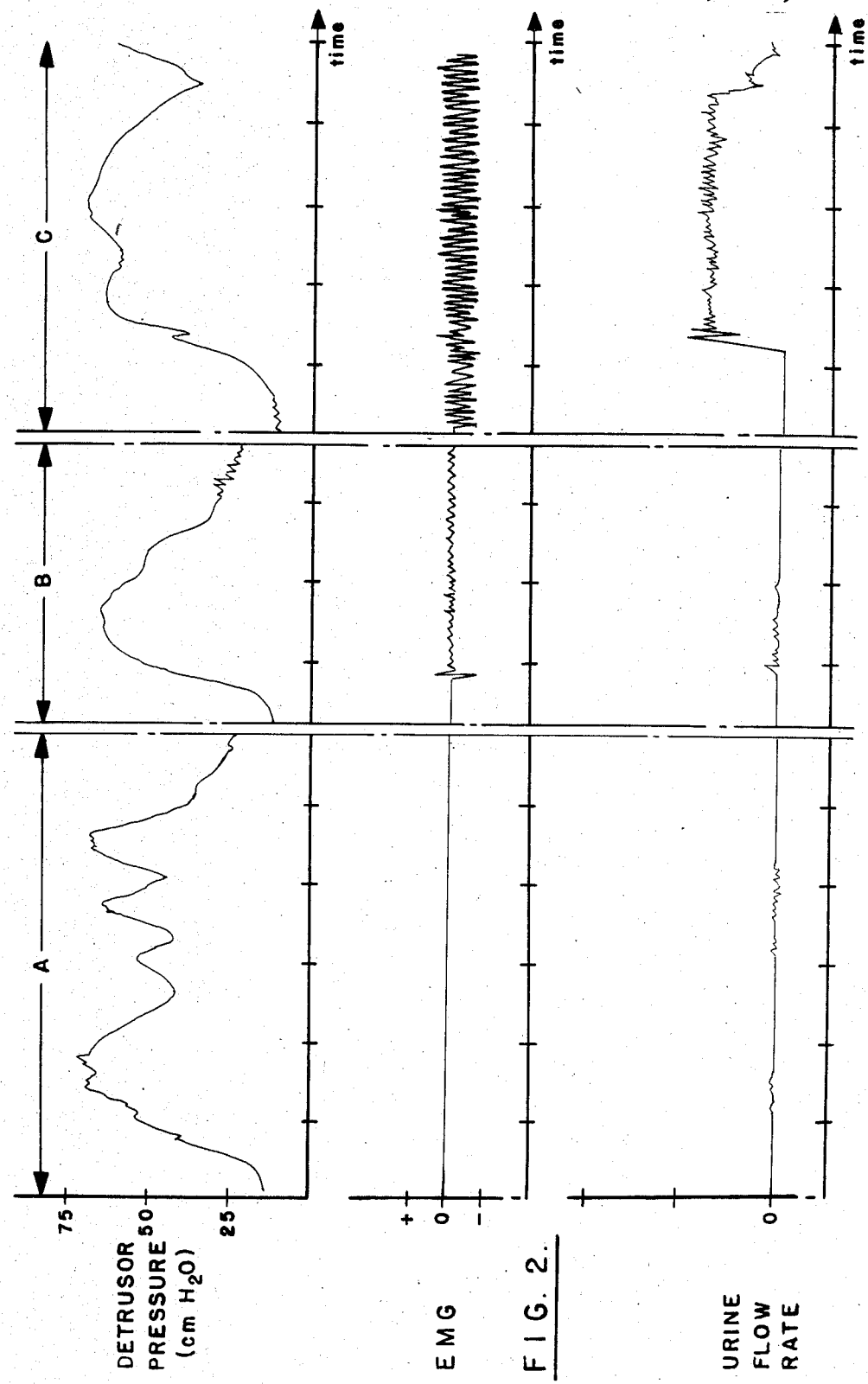
FIG. 2 is a graph showing data taken from the same subject used in FIG. 1, after taking a dose of 400 mg of thiphenamil hydrochloride.

The same subject was then monitored after a 400 mg dose of thiphenamil hydrochloride and the measurements were plotted in FIG. 2. Three segments of a polygraph recording are shown at the bladder capacity and conditions described in FIG. 1. As can be seen, the detrusor pressures in segments A and B in FIG. 2 are considerably higher than the corresponding values shown in FIG. 1.

Figure 3:
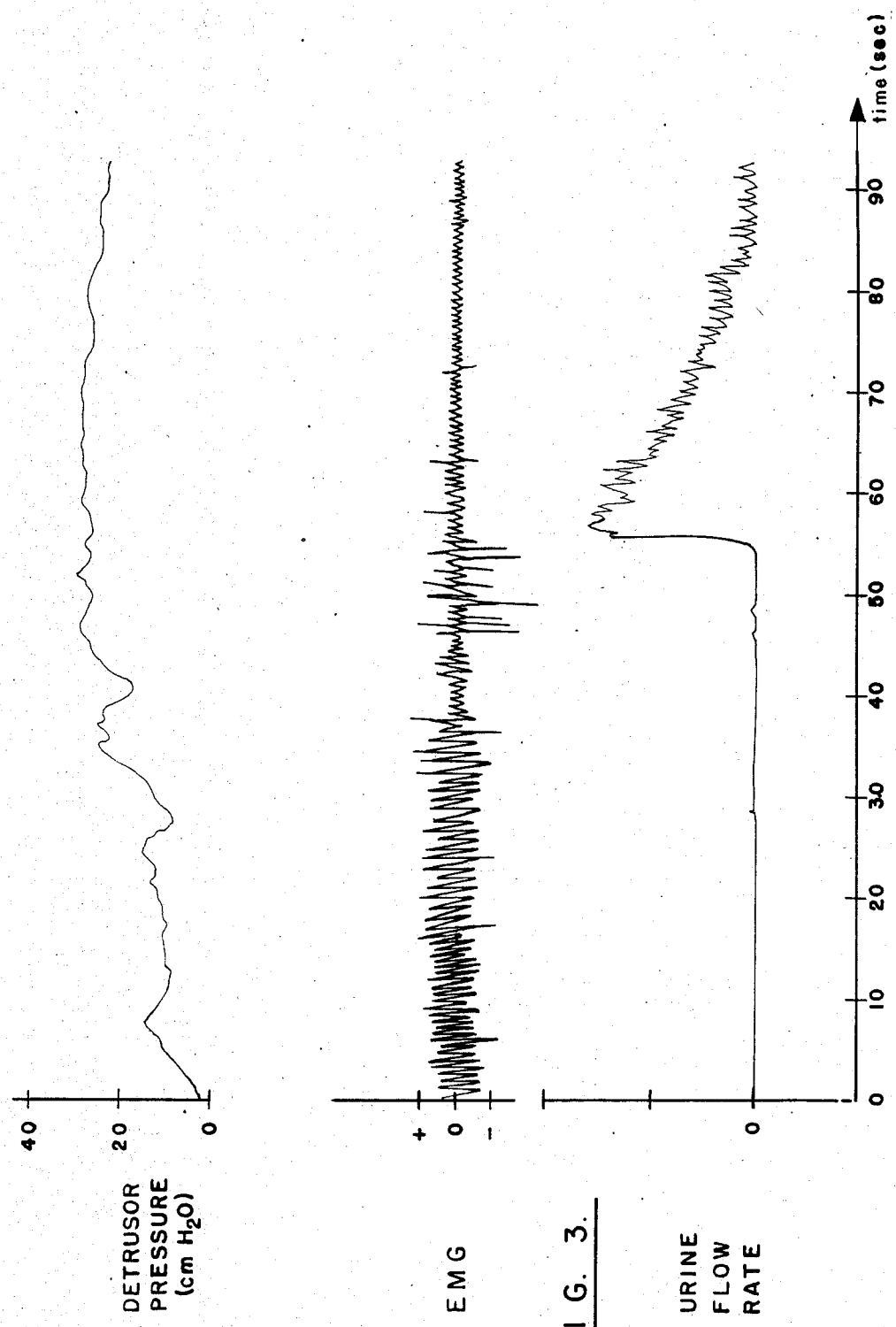
FIG. 3 is a graph showing data taken from a subject having an unstable detrusor.

FIG. 3 illustrates the voiding phase of the cystometrogram for a subject having an unstable detrusor muscle. Spontaneous detrusor contractions are shown to precipitate voiding at a bladder urine volume of about 210 ml. The onset of voiding is associated with involuntary contractions (series of detrusor pressure peaks between 0 and 50 seconds) that are suppressed by increased EMG activity. The voiding was voluntary and complete with no residual urine volume.

Figure 4:
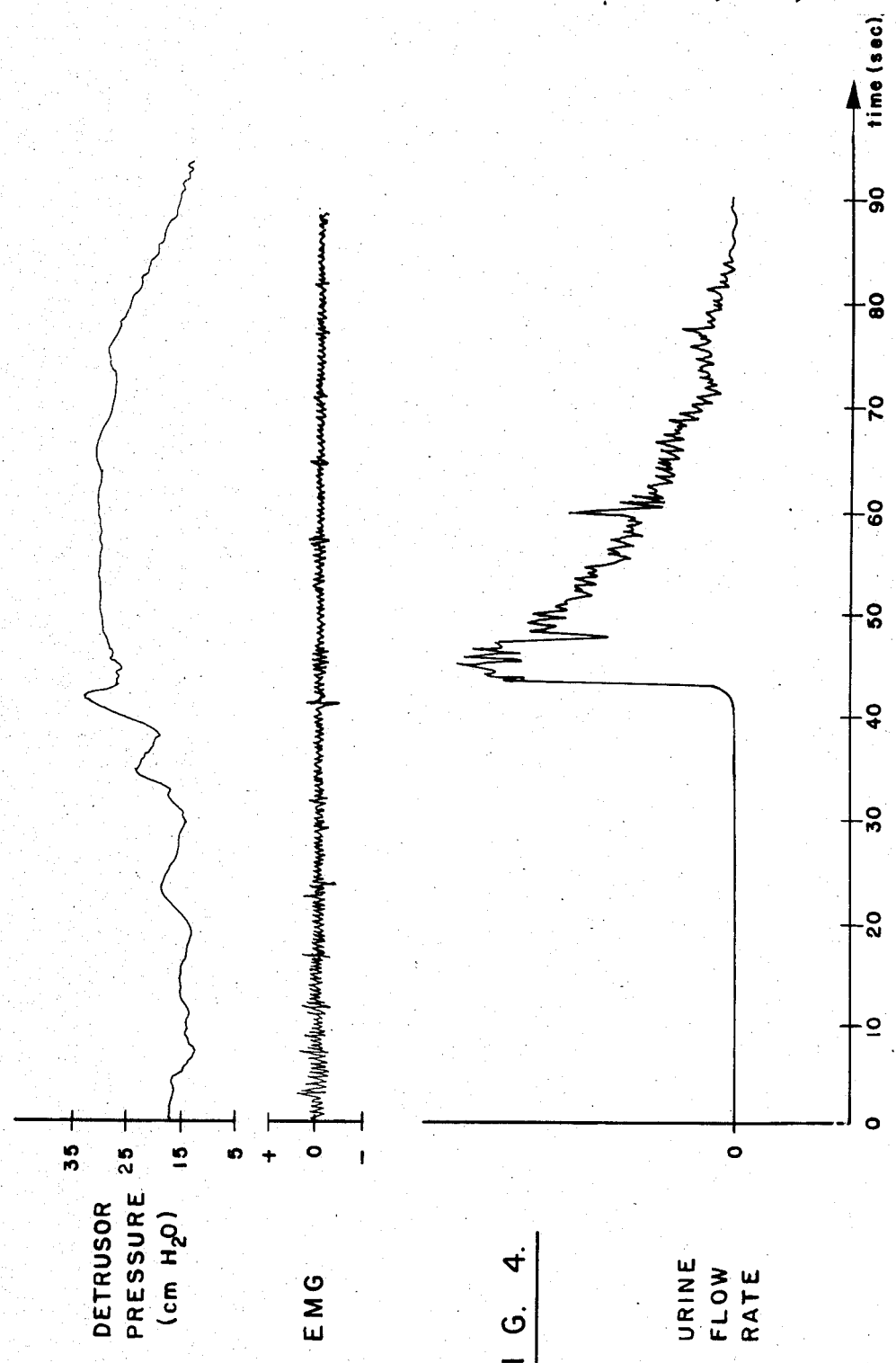
FIG. 4 is a graph showing data taken from the same subject used in FIG. 3, after having taken a 400 mg dose of thiphenamil hydrochloride 30 minutes prior to recording.

The same subject used in FIG. 3 was monitored, and the results traced, in FIG. 4 after being given a 400 ml dose of thiphenamil hydrochloride 30 minutes prior to recording. The polygraph shows that the pattern of destrusor instability (i.e., the series of increasing peaks in the detrusor pressure during the time leading up to voiding) observed under the control conditions illustrated in FIG. 3 has shifted significantly to the right as well as a general decrease in the height of those peaks. Hence, there is really only a significant detrusor pressure peak immediately before the onset of voiding.

As can be seen from the EMG tracing in FIG. 4, the range of fluctuations is greatly decreased indicating that the detrusor instability is nearly eliminated. In FIG. 4, voiding was voluntary and complete.

TABLE I

Stable Detrusor: Urodynamic parameters of the filling and voiding phase of the bladder under control conditions and also with 400 mg and 800 mg thiphenamil hydrochloride.

|  | Control | Thiphenamil Hydrochloride (400 mg) | Thiphenamil Hydrochloride (800 mg) |
|---|---|---|---|
| Compliance | 0.003 ± 0.001 | 0.002 ± 0.001 | 0.0025 ± 0.003 |
| V (1st sense) | 281 ± 126 (21) | 314 ± 99 (19) | 298 ± 67.6 (11) |
| V (Urge) | 525 ± 200 (21) | 551 ± 195 (19) | 381 ± 61 (11) |
| V (max) | 552 + 168 (21) | 581 + 155 (19) | 436 ± 165 (11) |
| P (opening) | 29.9 ± 14.0 (21) | 25.4 ± 13.3 (19) | 39.1 ± 12.2 (7) |
| P (max flow) | 36.7 ± 15.8 (21) | 37.9 ± 9.1 (19) | 49.5 ± 14.8 (11) |
| P (voiding) | 41.3 ± 15.5 (21) | 37.2 ± 16 (20) | 65.1 ± 19.1 (11) |
| Q (max) | 16.9 ± 4.6 (21) | 16.7 ± 4.4 (21) | 27.7 ± 9.0 (8) |
| R.U. | 69.3 ± 83.1 (18) | 132.3 ± 121.4 (18) | 95.0 ± 72.2 (9) |

Wherein:
1. Compliance is the compliance of the detrusor muscle in liters/cm $H_2O$.
2. V (1st sense) is the bladder urine volume in ml's at the patient's first sensation to urinate.
3. V (Urge) is the bladder urine volume in ml's at the patient's urge to urinate.
4. V (max) is the maximum bladder urine volume in ml's.
5. P (opening) is the bladder pressure at the patient's initiating urination in cm $H_2O$.
6. P (max flow) is the bladder pressure at maximum urine flow rate in cm $H_2O$.
7. P (voiding) is the bladder voiding pressure in cm $H_2O$.
8. Q (max) is the maximum urine flow rate in ml/sec.
9. R.U. is the residual or left over bladder urine volume in ml's.
10. (n) is the number of measurements taken, i.e. sample size.

TABLE II

Stable Detrusor: Maximum isometric pressure as a function of bladder volume under control conditions and also with 400 mg and 800 mg of thiphenamil hydrochloride.

|  | Control | Thiphenamil Hydrochloride (400 mg) | Thiphenamil Hydrochloride (800 mg) |
|---|---|---|---|
| I (100) | 36.1 ± 26.9 (10) | 63.0 ± 27.1 (13) | 74 ± 34.6 (6) |
| I (200) | 37.9 ± 23.4 (12) | 51.9 ± 26.0 (14) | 65.0 ± 37.8 (7) |
| I (300) | 35.9 ± 12.9 (8) | 50.3 ± 25.8 (12) | 63.4 ± 26.2 (7) |
| I (400) | 37.2 ± 17.9 (11) | 46.6 ± 19.5 (10) | 50.0 ± 27.5 (6) |
| I (500) | 36.8 ± 23.7 (9) | 30.1 ± 15.6 (8) | 34.0 ± 14.4 (2) |
| V (1st sense) | 316 ± 147 (18) | 358 ± 106 (18) | 253.3 ± 96.9 (6) |
| V (Urge) | 503 ± 138 (18) | 467 ± 94 (18) | 385 ± 74.6 (7) |
| V (Max) | 515 ± 162 (13) | 544 ± 151 (11) | 425 ± 82 (10) |

Wherein:
1. I (100 etc.) is the maximum bladder isometric pressure at a bladder urine volume of 100, 200 etc. ml's in cm $H_2O$.
2. V (1st sense) is the bladder urine volume in ml's at the patient's first sensation to urinate.
3. V (Urge) is the bladder urine volume in ml's at the patient's urge to urinate.
4. V (max) is the maximum bladder urine volume in ml's.
5. (n) is the number of measurements taken, i.e. sample size.

TABLE III

Unstable Detrusor: Urodynamic parameters of the filling and voiding phase of the bladder under control conditions and also with 400 mg and 800 mg of thiphenamil hydrochloride.

|  | Control | Thiphenamil Hydrochloride 400 mg | Thiphenamil Hydrochloride 800 mg |
|---|---|---|---|
| Compliance | 0.003 ± 0.001 | 0.002 ± 0.001 | 0.0027 ± 0.0004 |
| V (1st sense) | 217 ± 202 (4) | 270 ± 99 (3) | 275 ± 35 (3) |
| V (Urge) | 345 ± 209 | 345 ± 191 | 325 ± 35 (2) |
| V (max) | 398 ± 171 (3) | 440 ± 57 (2) | 499 ± 177 (3) |
| P (opening) | 38 ± 17 | 30 ± 12 (4) | 44 ± 11.3 (2) |
| P (maxflow) | 44.3 ± 3.1 (3) | 44.0 ± 4.4 (3) | 55.3 ± 7.0 (3) |
| P (voiding) | 53 ± 18 (4) | 47 ± 7 (4) | 52.7 ± 6.4 (3) |
| Q (max) | 18.2 ± 1.2 | 15 ± 1.9 | 18.0 ± 1.8 (3) |
| R.U. | 18 ± 22 (3) | 140 ± 85 (2) | 27.5 ± 3.5 (3) |

Wherein:
1. Compliance is the compliance of the detrusor muscle in liters/cm $H_2O$.
2. V (1st sense) is the bladder urine volume in ml's at the patient's first sensation to urinate.
3. V (Urge) is the bladder urine volume in ml's at the patient's urge to urinate.
4. V (max) is the maximum bladder urine volume in ml's.
5. P (opening) is the bladder pressure at the patient's initiating urination in cm $H_2O$.
6. P (max flow) is the bladder pressure at maximum urine flow rate in cm $H_2O$.
7. P (voiding) is the bladder voiding pressure in cm $H_2O$.
8. Q (max) is the maximum urine flow rate in ml/sec.
9. R.U. is the residual or left over bladder urine volume in ml's.
10. (n) is the number of measurements taken, i.e. sample size.

TABLE IV

Unstable detrusor: Maximum isometric pressure as a function of bladder volume under control conditions and also with 400 mg and 800 mg of thiphenamil hydrochloride.

|  | Control | Thiphenamil Hydrochloride (400 mg) | Thiphenamil Hydrochloride (800 mg) |
|---|---|---|---|
| I (100) | 32 ± 13 (3) | 73 ± 39 (14) | 78 ± 53 |
| I (200) | 42 ± 35 (4) | 44 ± 14 (3) | 62 ± 57 |
| I (300) | 35 ± 13 | 75 ± 5 (2) | 96 (1) |
| V (1st sense) | 217 ± 143 (4) | 270 + 99 (4) |  |
| V (urge) | 320 ± 170 (4) | 355 ± 53 (4) | 423 ± 27.5 |

Wherein:
1. Compliance is the compliance of the detrusor muscle in liters/cm $H_2O$.
2. V (1st sense) is the bladder urine volume in ml's at the patient's first sensation to urinate.
3. V (Urge) is the bladder urine volume in ml's at the patient's urge to urinate.
4. V (max) is the maximum bladder urine volume in ml's.
5. P (opening) is the bladder pressure at the patient's initiating urination in cm $H_2O$.
6. P (max flow) is the bladder pressure at maximum urine flow rate in cm $H_2O$.
7. P (voiding) is the bladder voiding pressure in cm $H_2O$.
8. Q (max) is the maximum urine flow rate in ml/sec.
9. R.U. is the residual or left over bladder urine volume in ml's.
10. (n) is the number of measurements taken, i.e. sample size.
11. I (100 etc.) is the maximum bladder isometric pressure at a bladder urine volume of 100, 200 etc. mls, in cm $H_2O$.

I claim:

1. A method for simultaneously inhibiting detrusor muscle contraction during bladder filling and increasing the force of voluntary contraction of the detrusor muscle during bladder emptying comprising administering to a patient requiring such treatment an effective amount of a di-N-substituted aminoethyl ester of diphenylthioacetic acid having the formula:

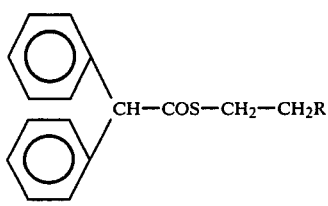

in which R represents a disubstituted amino radical of the group consisting of the diethylamino group, the morpholino group and the piperidino group.

2. The method as described in claim 1, wherein the di-N-substituted aminoethyl ester of diphenylthioacetic acid is administered in a dosage of from about 0.7 to about 11.4 mg per kilogram of body weight.

3. The method as described in claim 1, wherein the di-N-substituted aminoethyl ester of diphenylthioacetic acid is administered in a preferred dosage of from about 1.4 to about 5.7 mg per kilogram of body weight.

4. The method as described in claim 1, wherein the di-N-substituted aminoethyl ester of diphenylthioacetic acid is administered in a more preferred dosage of from about 2.8 to about 5.7 mg per kilogram of body weight.

5. The method as described in claim 1, wherein the di-N-substituted aminoethyl ester of diphenylthioacetic acid is combined with a pharmaceutically acceptable carrier.

6. A method for simultaneously increasing voluntary detrusor contraction during bladder emptying and decreasing detrusor muscle contraction during bladder filling causing no significant increase in bladder capacity and without leaving or accumulating any foreign substances in human body tissues comprising administering to a patient a therapeutically effective amount of a di-N-substituted aminoethyl ester of diphenylthioacetic acid having the formula:

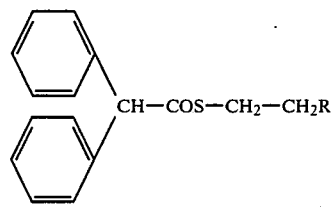

in which R represents a disubstituted amino radical of the group consisting of the diethylamino group, the morpholino group and the piperidino group.

* * * * *